(12) United States Patent
Young

(10) Patent No.: US 6,299,606 B1
(45) Date of Patent: Oct. 9, 2001

(54) URINE COLLECTION DEVICE

(76) Inventor: Michael J. Young, 680 N. Lake Shore Dr., #424, Chicago, IL (US) 60611

( * ) Notice: Subject to any disclaimer, the term of this patent is extended or adjusted under 35 U.S.C. 154(b) by 0 days.

(21) Appl. No.: 09/270,032

(22) Filed: Mar. 16, 1999

(51) Int. Cl.$^7$ .................................................. A61F 5/44
(52) U.S. Cl. ............................................ 604/329; 604/317
(58) Field of Search .................................. 604/317, 326, 604/329, 331; 600/573, 574, 576; 422/102, 61; 4/479, 480, 144.1, 144.3, 455

(56) References Cited

U.S. PATENT DOCUMENTS

| 3,680,543 | 8/1972 | Cox . |
| 3,711,871 | 1/1973 | Sherin . |
| 3,777,739 | 12/1973 | Raitto . |
| 3,811,136 | 5/1974 | Whitney et al. . |
| 4,305,161 | 12/1981 | Diaz . |
| 4,559,649 | 12/1985 | Burnett . |
| 4,568,339 | * 2/1986 | Steer .................................... 604/329 |
| 4,569,090 | 2/1986 | Muller . |
| 4,936,838 | * 6/1990 | Cross et al. ........................... 604/329 |
| 5,069,878 | 12/1991 | Ehrenkranz . |
| 5,422,076 | * 6/1995 | Jones .................................... 422/102 |
| 5,571,095 | 11/1996 | Lu . |
| 5,632,736 | * 5/1997 | Block ................................... 604/329 |
| 5,797,147 | * 8/1998 | Young et al. ......................... 4/144.1 |
| 5,842,233 | * 12/1998 | Broden ................................. 4/144.1 |
| 5,894,608 | * 9/1999 | Birbara ................................ 4/144.3 |
| 5,920,916 | * 7/1999 | Norton ................................. 4/144.3 |
| 5,956,782 | * 9/1999 | Olguin ................................. 4/454 |

* cited by examiner

Primary Examiner—Manuel Mendez
(74) Attorney, Agent, or Firm—Marshall, O'Toole, Gerstein, Murray & Borun

(57) ABSTRACT

A urine collection device for women has a bowl with sides that bow inwardly to provide a comfortable fit while minimizing spillage. The bowl has an aperture through which urine can pass to a removable specimen jar. An elongated handle extends from the front of the bowl, and is provided with fingergrips on its bottom edge. The device can be molded from plastic, permitting it to be sanitized and reused.

14 Claims, 5 Drawing Sheets

URINE COLLECTION DEVICE

TECHNICAL FIELD

The present invention relates generally to urine collection devices, and more particularly to hand-held urinal collection devices for women.

BACKGROUND ART

In the medical and health care fields, it is commonly desirable to obtain a urine specimen from an individual. Conventionally, urine collection devices are containers with a small opening, and it is commonly a problem for women to provide a specimen in such containers. A variety of different types of devices have been patented in efforts to address this problem. None, however, enjoys commercial success in modern medical facilities.

Since as early as the 1930's, efforts have been made to design funnel-like devices that can be attached to a specimen container to facilitate use by women. Dwork, U.S. Pat. Nos. 1,928,170; Hill, 3,131,403; Gibson, 3,171,136 all show early efforts at such devices.

Whitney et al., U.S. Pat. Nos. 3,811,136, and Burnett, 4,559,649, hint that one problem with such early funnels was that their bulky shape made them uncomfortable for women to use properly. The solution by Whitney et al. was to provide a collapsible funnel that is "soft enough to conform to the GU area"(col. 1, lines 31–32). The less-costly solution proposed by Barnett was to "compensat[e] for [women's] difficulty by following the natural contours of the perineum allowing the funnel to be placed closely to the subject's body."(Col. 4, line 68–col. 5 line 2). While Barnett proposed to accomplish a better fit by configuring the funnel with parallel lateral sides that curve upwardly (col. 4, lines 50–63), her design has not found widespread acceptance.

Even more recently, it has been proposed to abandon efforts to help women to provide urine specimens in the same kind of small containers that men conventionally use, and instead to provide a larger container that can be more easily used by women. Jones, U.S. Pat No. 5,422,076, discloses such a device. However, physicians are likely to be unwilling to stock two separate types of specimen jars, or to ask their male patients to use larger and more-expensive jars.

SUMMARY OF THE INVENTION

The applicant has developed an inexpensive urine collection device that can be used more easily and successfully than any previously-known device. The device comprises a bowl with an aperture, integral means for attaching a conventional specimen jar beneath the bowl to receive urine passing through the aperture, and an elongated handle extending from the front of the bowl.

One important aspect of the invention is the configuration of the bowl. Rather than being straight or bowing laterally outwardly between a woman's legs, the bowl has an inward bow. Curved sides on the bowl bow inwardly from a pair of forward inflection points to a pair posterior inflection points and, at the narrowest point, form a waist section about 3 inches wide.

The benefits of the invention can be better understood by reviewing the following detailed description and drawings, in which:

DESCRIPTION OF THE PREFERRED EMBODIMENT

Figure 1:
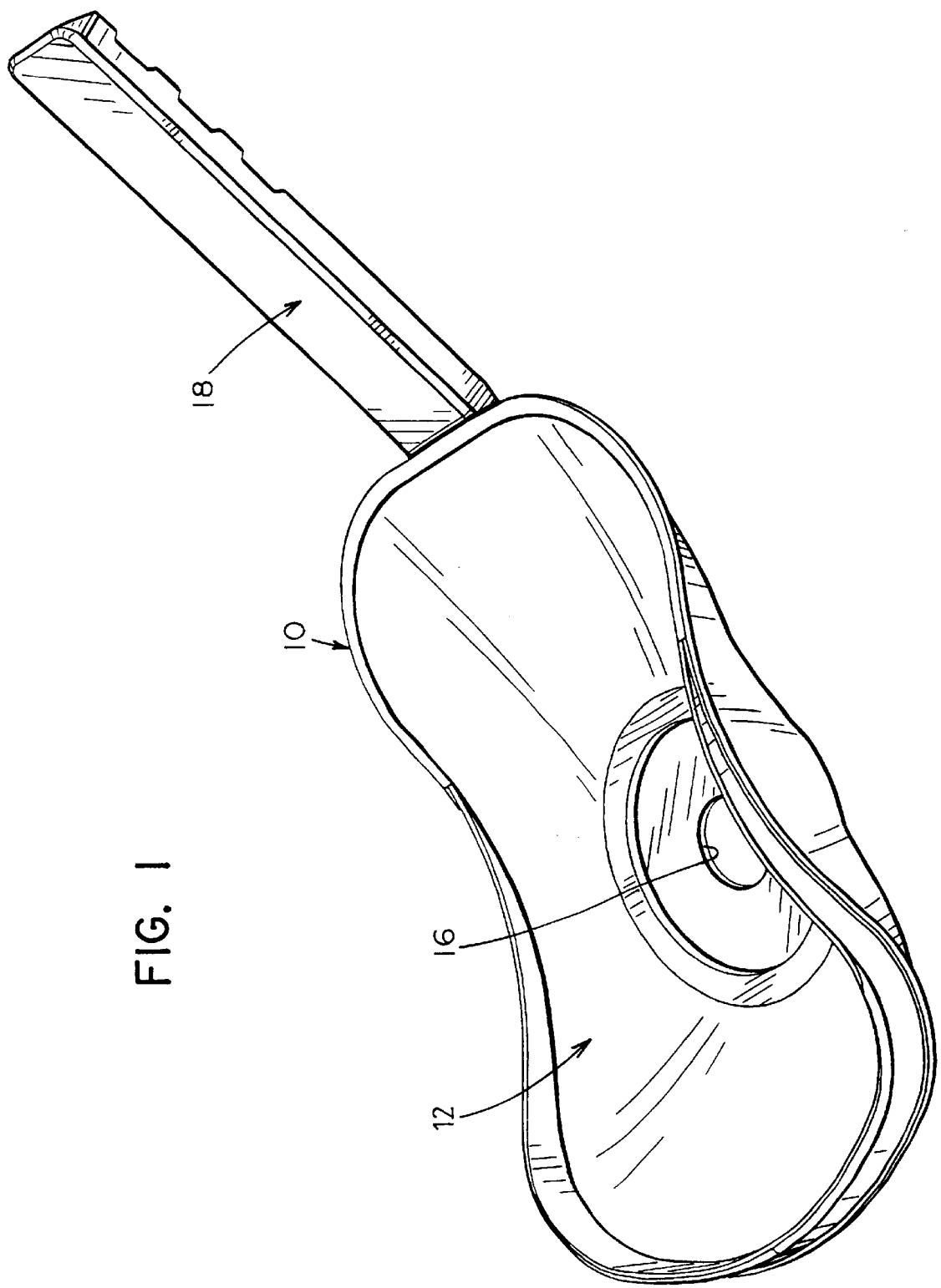
FIG. 1 is a perspective view of a urine collection device in accordance with the present invention.

FIG. 1 shows a preferred embodiment of a urine collection device 10 in accordance with the present invention. The urine collection device comprises a bowl 12 with an integral connector 14 (FIG. 2) for attaching a conventional specimen jar beneath the bowl, an aperture 16 above the attachment means, and a handle 18. The device is preferable made of molded plastic. This allows the device to be fabricated inexpensively, and provides sufficient durability to allow the product to be sanitized and reused.

Figure 2:
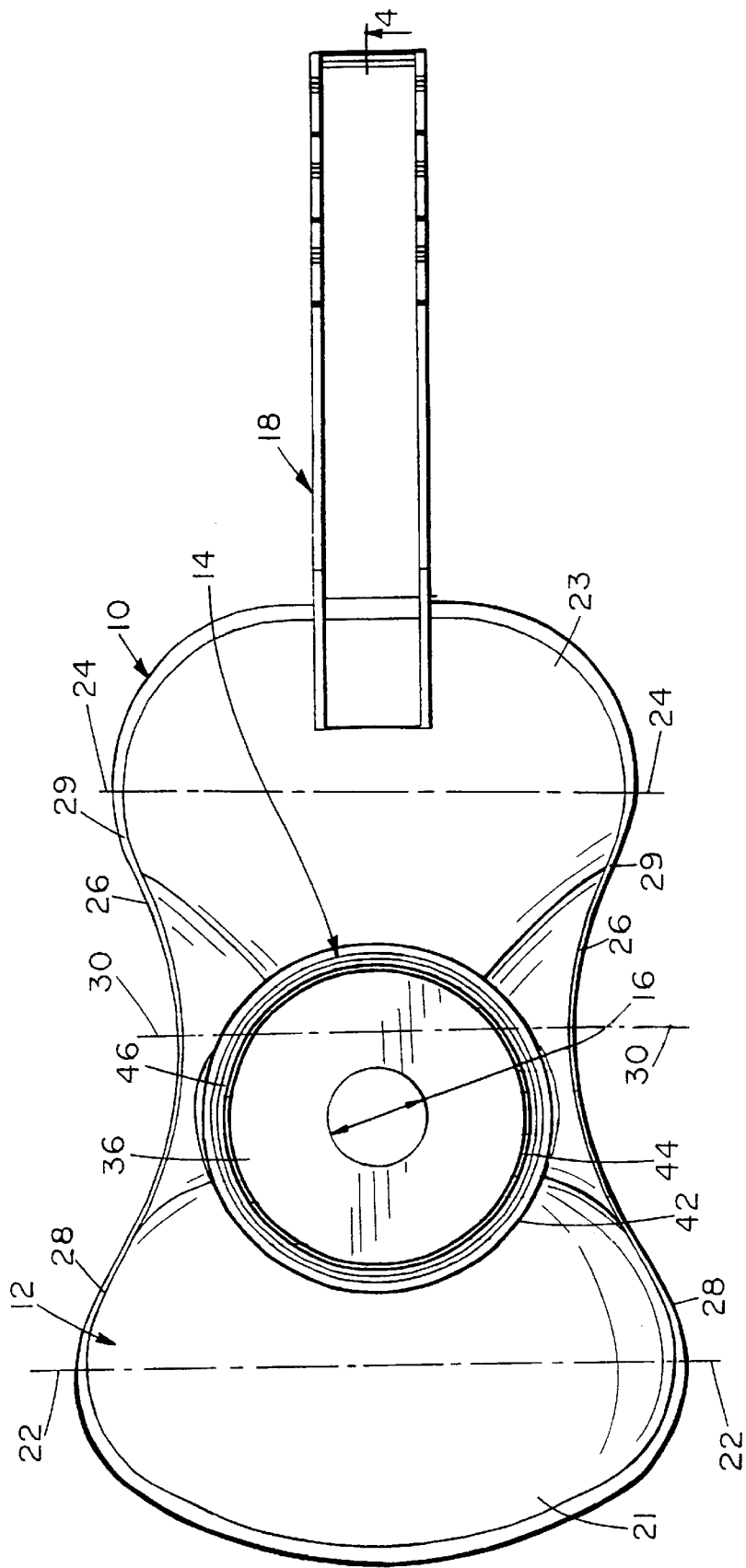
FIG. 2 is a bottom plan view of the urine collection device of FIG. 1.

As seen in FIG. 2, the bowl 12 of the device 10 is about 7 inches long and has an hourglass shape designed to minimize the chance of spillage, while permitting comfortable use by a woman. The hourglass shape is characterized by posterior portion 21 that is about 4½ to about 5 inches wide at its widest section 22 and a forward portion 23 that is about 4 inches wide at its widest section 24. The width of these portions of the device minimize the chance of spillage. Curved sides 26 on the bowl bow inwardly from posterior inflection points 28 near the widest section 22 of the posterior portion to forward inflection points 29 near the widest section 24 of the forward portion 23. As shown, the sides of the bowl form a continuous curve through the inflection points, minimizing the chance of scrapes when the device is being used. Alternatively, the inflection points could take the form of an angle at which the sides of the bowl begin to diverge inwardly. The inward curve of the sides forms a waist section 30 that is about 3 inches wide. The inwardly-curved sides also facilitate proper placement of the device.

Figure 3:
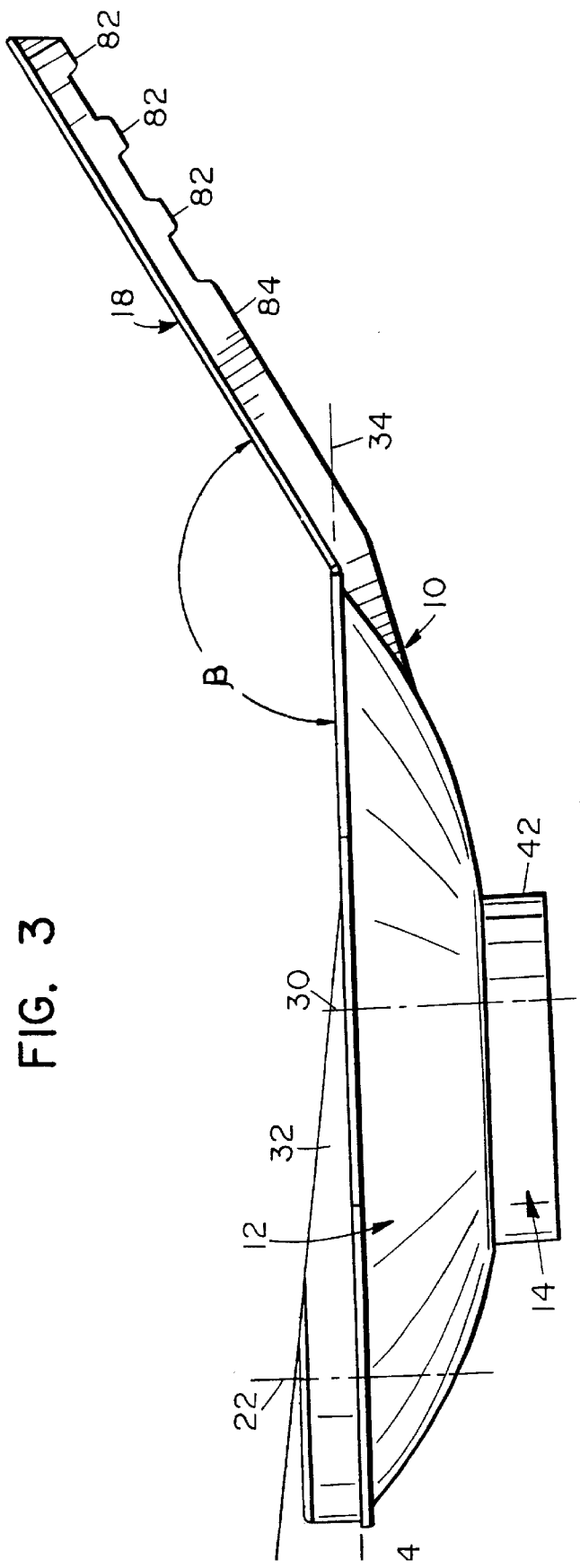
FIG. 3 is a side view.

Preferably, a raised skirt 32 (FIG. 3) extends upwardly from a longitudinal axis 34 of the device in the posterior portion 21. As illustrated, the skirt begins near the waist section 30 and rises at an angle a of 5 to 10 degrees until it reaches a maximum height of about half an inch near the widest section 22 of the posterior portion 21 of the bowl 12. This configuration of the skirt helps to assist in proper positioning of the device, and also helps to reduce spillage from splashing.

As illustrated (FIG. 2), the rearward inflection points 28 are about 4 inches apart, and the forward inflection points 29 are about 3¾ inches apart. The forward inflection points are located about 1½ inches forward of the waist section 30, while the rearward inflection points are located about 2 inches behind the waist section.

In other embodiments of the invention, the dimensions could vary by up to about 25% of those provided above.

Figure 4:
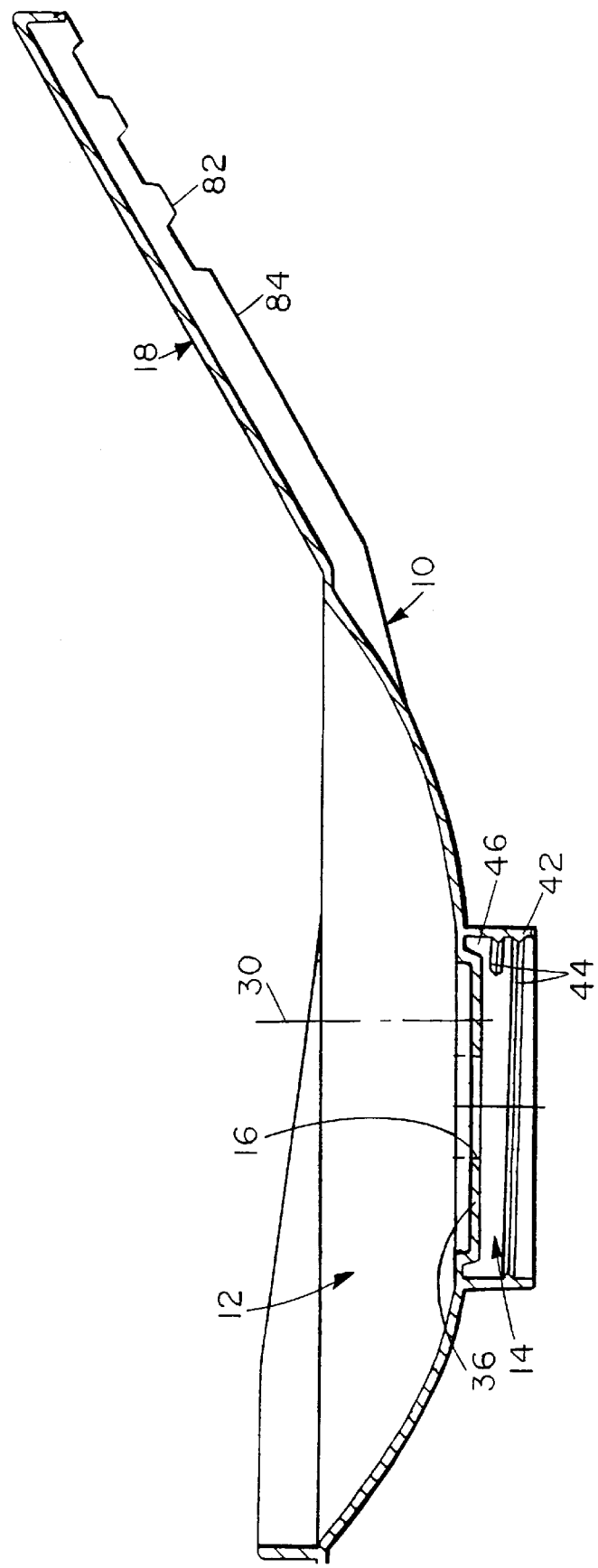
FIG. 4 is a cross-sectional side view taken through lines 4—4 of FIG. 2.
Figure 5:
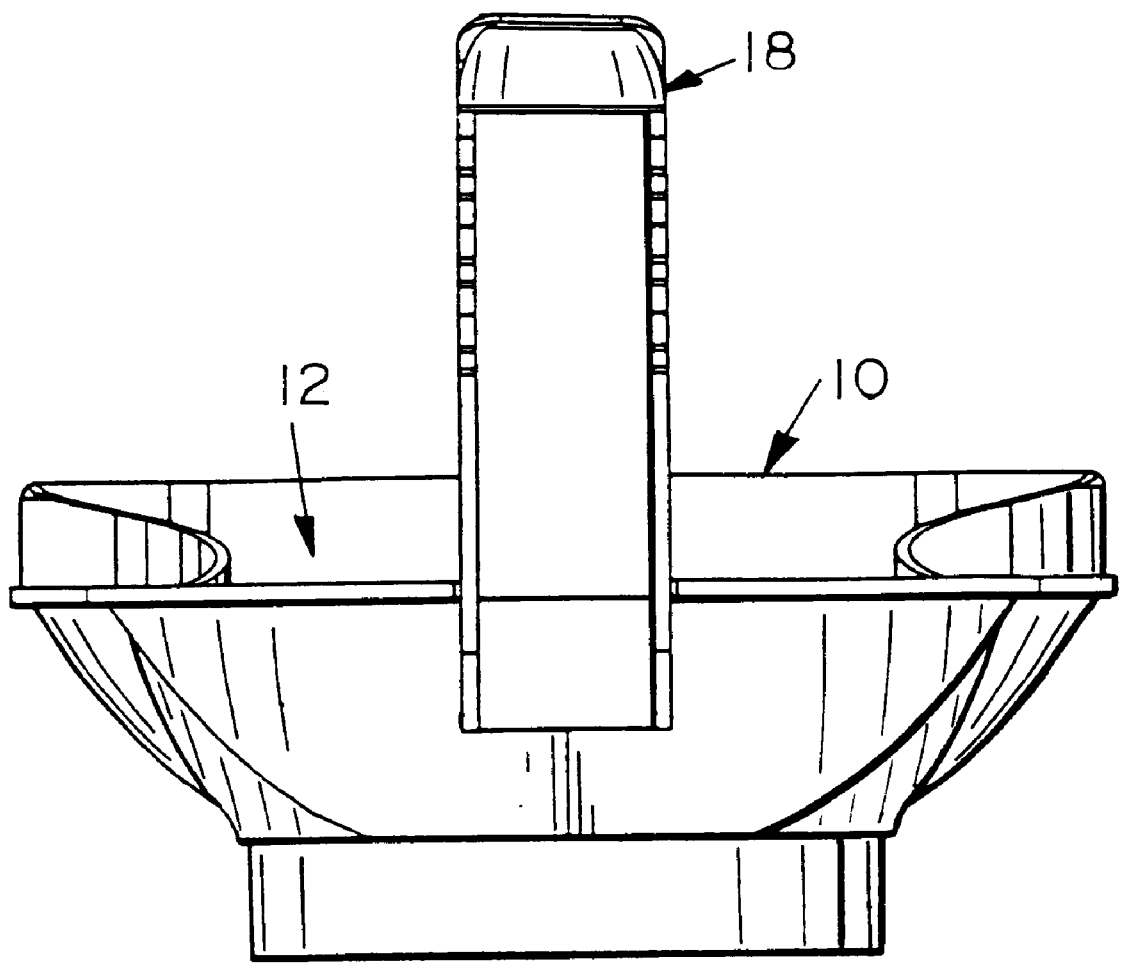
FIG. 5 is an end view.

The connector 14 (FIGS. 3 and 4) is integrally formed on the bottom of the bowl 12 to enable a conventional specimen jar to be attached to the device 10 beneath the bowl. After use, the specimen jar is removed for analysis or storage, and the device 10 can be sterilized and reused by attaching another specimen jar.

As illustrated, the connector 14 takes the form of a downward collar 42 provided with internal threads 44. The collar is continuous around its periphery, and can completely encircle the top of an attached specimen jar, minimizing the chance of leakage. To accommodate a conventional specimen jar, the outside diameter of the collar is greater than about 2½ inches. To achieve good collection with a minimal amount of leakage, the connector may be centered between about ½ and 1 inch behind the waist section 30 of the bowl 12. The type of connector is not important to the invention, and other types of connectors that provide a secure attachment of a specimen jar to the device could also be used.

As illustrated, a flange 36 on the bottom of the bowl 12 defines the aperture 16 in the bowl above the connector 14. As illustrated, the aperture is circular with a diameter of approximately ¾ of an inch, and has a cross-sectional area significantly less than the cross-sectional area of a conventional specimen jar. When a specimen jar is connected to the device, the flange covers a portion of the opening on the top of the specimen jar, and thus can serve to limit spillage of urine from the jar after it has been filled. An annular recess 46 (FIG. 4) between the flange 36 and the collar 42 on the connector 14 can also accommodate the top of a specimen jar, further reducing the chance of spilling.

The elongated handle 18 extends from the front of the bowl 12, providing a convenient way for a woman to hold the device 10 while it is in use. As illustrated, the handle is between about 4 and about 5 inches long and forms at an angle β of about 150 degrees with respect to the longitudinal axis 34 of the device. Fingergrips 82 on the bottom edge 84 of the handle help to assist women in recognizing that the handle can be easily grasped with the palm facing upwards, and the thumb away from the body.

This description is illustrative only, and is for the purpose of teaching those skilled in the art the best mode of carrying out the invention. Numerous modifications and alternative embodiments of the invention will be apparent to those skilled in the art, without departing from the spirit of the invention

I claim:

1. A urine specimen collection device comprising:

a bowl with an aperture;

integral means for attaching a specimen jar to receive urine passing through the aperture;

rigid, curved sides on the bowl the bow inwardly from a pair of forward inflection points to a pair posterior inflection points, forming a waist section that is about 3" wide;

an elongated handle extending from the front of the bowl.

2. The urine specimen collection device of claim 1, in which:

a section of the bowl forward of the waist section has a width of about 4 inches.

3. The urine specimen collection device of claim 1, in which:

the width of the bowl about 2 inches forwardly of the center of the attaching means is about 3½ inches.

4. The urine specimen collection device of claim 1, in which:

a section of the bowl rearwardly of the waist section has a width of from about 4 to about 5 inches.

5. The urine specimen collection device of claim 1, in which:

the width of the bowl about 2 inches behind the center of the attaching means is from about 4 to about 5 inches.

6. The urine specimen collection device of claim 1, in which the bowl is at least about 6 inches long, with an posterior portion and a forward portion, the posterior portion having a wider maximum width than the forward portion.

7. The urine specimen collection device of claim 1, in which the attaching means is centered behind the waist section.

8. A urine specimen collection device of claim 1, in which the handle forms an angle of about 150 degrees with respect to a longitudinal axis of the device.

9. A urine specimen collection device of claim 1, in which the handle has a lower edge with fingergrips.

10. A urine specimen collection device of claim 1, in which the cross-sectional area of the aperture is less than about 1 square inch.

11. A urine specimen collection device of claim 1, and further comprising an annular recess between a flange defining the aperture in the bowl and an upper portion of a collar on the integral attaching means.

12. A urine specimen collection device of claim 1, in which the device is molded of plastic.

13. A urine specimen collection device comprising:

a bowl with an aperture;

integral means for attaching a specimen jar to receive urine passing through the aperture;

thin, curved sides on the bowl that bow inwardly from a pair of forward inflection points to a pair posterior inflection points, forming a waist section that is about 3" wide;

an elongated handle extending from the front of the bowl.

14. A urine specimen collection device comprising:

a bowl with an aperture;

integral means for attaching a specimen jar to receive urine passing through the aperture;

curved sides that extend upwardly from the widest part of the bowl and bow inwardly from a pair of forward inflection points to a pair posterior inflection points, forming a waist section that is about 3" wide;

an elongated handle extending from the front of the bowl.

* * * * *